United States Patent [19]

deJong et al.

[11] 4,239,923

[45] Dec. 16, 1980

[54] LINALOOL FROM DIMETHYLOCTADIENE VIA EPOXIDE AND CYCLOOCTENOL

[75] Inventors: Aaldert J. deJong; Hendricus J. Heijmen, both of Amsterdam, Netherlands

[73] Assignee: Shell Oil Company, Houston, Tex.

[21] Appl. No.: 90,769

[22] Filed: Nov. 2, 1979

Related U.S. Application Data

[62] Division of Ser. No. 844,956, Oct. 25, 1977.

[30] Foreign Application Priority Data

Nov. 1, 1976 [GB] United Kingdom ............... 45309/76

[51] Int. Cl.³ .............................................. C07C 33/02
[52] U.S. Cl. ................................................ 568/875
[58] Field of Search ........................................ 568/875

[56] References Cited

U.S. PATENT DOCUMENTS

| | | | |
|---|---|---|---|
| 3,028,431 | 4/1962 | Webb | 568/875 |
| 3,060,237 | 10/1962 | Bain | 568/875 |
| 3,240,821 | 3/1966 | Ohloff et al. | 568/875 |
| 4,157,451 | 6/1979 | Ohloff et al. | 568/875 |

OTHER PUBLICATIONS

Watanabe et al., "J. Appl. Chem. Biotechnol.", vol. 24, No. 11, Nov. 1974, pp. 639–643.

*Primary Examiner*—Joseph E. Evans

[57] ABSTRACT

Novel cyclooctene derivatives of the formula:

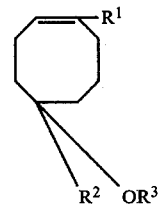

in which $R^1$ and $R^2$ each represents an alkyl group and $R^3$ is hydrogen or an acyl group are disclosed along with their use as aroma chemicals and/or aroma chemical precursors and processes for their preparation.

2 Claims, No Drawings

LINALOOL FROM DIMETHYLOCTADIENE VIA EPOXIDE AND CYCLOOCTENOL

This is a division, of application Ser. No. 844,956, filed Oct. 25, 1977.

BACKGROUND OF THE INVENTION

This invention relates to a novel class of cyclooctene derivatives which are of interest in the aroma chemical field and to processes for their preparation. More particularly, this invention is directed to a particular class of hydroxy- or carbonyl-substituted cyclooctenes which are useful as aroma chemicals and/or intermediates in the synthesis of certain known aroma chemicals e.g., alpha-linalool, as well as processes for their preparation using synthetically derived starting materials--i.e., mixtures of dialkyl cyclooctadienes obtained, for example, by cyclodimerization of isoprene.

A variety of hydroxy- and carbonyl-substituted organic compounds are known in the art to possess aroma properties which are useful in the perfumery field. While some of these organic compounds can be, and are, produced commercially from synthetic or industrial sources, a significant portion of the commercial market still relies on natural products such as terpene and terpene derivatives. Further, even though a variety of established aroma compounds including hydroxyaldehydes, esters, aldehydes, ketones and alcohols can be derived from these synthetic sources, there still exists a continuing need for new compounds which accent particular fragrances or other odorant properties in addition to more economic and convenient synthetic sources for the established compounds.

SUMMARY OF THE INVENTION

According to the invention, a novel class of hydroxy- and carbonyl substituted cyclooctenes have been found which are a high interest in the aroma chemical field either for their aroma properties or use as synthetically derived precursors or intermediates in the production of estblished aroma chemicals such as alpha-linalool. These novel cyclooctene derivatives are represented by the general formula I:

in which $R^1$ and $R^2$ each represents an alkyl group of 1 to 4 carbon atoms, and $R^3$ represents a hydrogen atom or an acyl group of up to 4 carbon atoms.

Additional advantages accrue for the novel cyclooctene derivatives of the invention in that they can be readily synthesized from industrial starting materials such as mixtures of dialkylcyclooctadienes available, for example from cyclodimerization of isoprene. Accordingly, these synthesis techniques comprise yet another aspect of the invention.

DESCRIPTION OF THE PREFERRED EMBODIMENTS

Preferred compounds of the above formula I are those in which $R^1$ and $R^2$ are methyl or ethyl groups. Most preferably $R^1$ and $R^2$ are both methyl groups. The acyl group represented by $R^3$ is preferably an acetyl group and therefore particularly preferred compounds according to formula I are 1,5-dimethylcyclooct-1-en-5-ol and its acetate ester.

According to the invention, a preferred method for the preparation of the compounds of formula I in which $R^3$ represents a hydrogen atom comprises the reduction of mono-epoxy compounds of the formula:

The reduction results in the formation of the tertiary alcohols represented by formula I in which $R^3$ is hydrogen. The formation of secondary alcohols and of saturated ring compounds, by reduction of the double bond in the ring is undesirable and therefore a reducing agent is used which selectively reacts with the epoxy group. Very suitable reducing agents in this respect are alkali metals, combined with amino compounds, a preferred combination being sodium in liquid ammonia. Lithium and potassium are also suitable. Various amino compounds are recommended, such as ethylene diamine, diethylamine, pyridine, hexamethylphosphoric acid triamide and the like. In addition, a solvent may be present, such a tetrahydrofuran and alcohols such as ethanol and tertiary butanol. The reduction is conveniently performed under reflux conditions and usually proceeds at temperatures in the range of $-50°$ to $+50°$ C., depending on the amino compound selected. The pressure is preferably about equal to atmospheric pressure, but higher pressures or subatmospheric pressures, e.g. 0.5 atmosphere, may be applied as well.

According to the invention, compounds of the formula II can be conveniently prepared by epoxidation of cyclooctadiene derivatives of formula:

The epoxidation of these cyclooctadiene derivatives is performed with a peroxy compound, preferably an alkyl hydroperoxide such as tert-butyl hydroperoxide in the presence of a catalyst selected from the class consisting of titanium and molybdenum to form a monoepoxide. A homogeneous epoxidation catalyst, e.g. $Mo(CO)_6$ may be used. However, a heterogeneous catayst, for example, a $TiO_2$/silica catalyst such as is described in British Pat. No. 1,249,079 is preferably used in this epoxidation step. Diluents, for example, liquid hydrocarbons such as cyclohexane may also be present. Preferred reaction temperatures are from 50° to 120° C.

In practice compounds of the formula III are often available in admixture with minor amounts of other dialkylcyclooctadienes. If desired such mixtures, e.g., a mixture obtained by cyclodimerization of isoprene, which mixture contains, in addition to 1,5-dimethylcyclooct-1,5-diene, a minor amount of the 1,6-dimethyl cyclooctadiene, can also be used as starting material. If this mixture is epoxidized and the product is subjected to a reduction as described above, and it has been observed, in particular when applying sodium in combination with liquid NH₃, that the desired tertiary alcohol of formula I (with R³ is hydrogen) is selectively formed from the 1,5-dialkyl compound, whereas the 1,6-dialkyl compound is reduced to a secondary alcohol thus allowing an easy separation by distillation.

Another preferred process for the preparation of compounds of formula I in which R³ represents a hydrogen atom comprises reacting a cyclooctadiene derivative of formula III with a mineral acid, followed by hydrolysis. The mineral acid is preferably a hydrogen halide, in particular HCl, although HBr is also suitable. In this manner mono-halocyclooctene derivatives are formed, the halogen atom being linked to the same carbon atom as one of the groups $R^1$ to $R^2$.

In the above mentioned process, the hydrohalogenation step can be carried out in the presence of a catalyst, e.g. a halide of a metal such as copper, zinc or tin. When a mono-chloro derivative is to be formed, preferred catalysts are cuprous chloride, zinc chloride or stannic chloride. However, this step can also be carried out in the absence of a catalyst. Suitable reaction temperatures are in the range of −30° to 150° C., preferably in the range of 10° to 70° C. If desired a solvent may be present, e.g. an alkane or a polar substance such as acetic acid, diethyl ether or tetrahydrofuran. The hydrolysis step is preferably carried out under basic conditions, e.g. by using an aqueous alkali or alkaline earth metal hydroxide, most preferably in the presence of a phase transfer catalyst such as a tetraalkylammonium halide. Preferably the hydrolysis is performed with the aid of a calcium compound such as calcium carbonate or, in particular, calcium hydroxide.

The compounds of formula I wherein R³ represents an acyl group of 1 to 4 carbon atoms may be prepared by esterification of the appropriate compound of formula I wherein R³ represents a hydrogen atom. This reaction is suitably carried out using conventional methods, e.g., heating the compound of formula I with a carboxylic acid anhydride, under conditions at which the excess carboxylic acid formed is removed by distillation. Alternatively, the ester may be obtained by forming the mono-halocyclooctene from the compound of formula III and treating this compound with a salt of the appropriate carboxylic acid, for example sodium acetate. It is also possible to convert the ester formed in this way to the alcohol by saponification.

The preferred compound of the invention, 1,5-dimethylcyclooct-1-en-5-ol, is of interest as a chemical intermediate. In particular the compound is isomeric with alpha-linalool (3,7-dimethylocta-1,6-dien-3-ol, an aroma chemical with a strong floral odor. The cyclic compound may be converted to alpha-linalool by thermal isomerization. Suitable isomerization temperatures are in the range of 350°–650° C., preferably in the range of 500° to 600° C. If desired, heat transferring means may be applied by filler bodies, for example copper bodies. The invention therefore includes the complete synthesis scheme wherein 1,5-dimethylcyclooct-1-en-5-ol prepared according to the above techniques is subsequently used to prepare alpha-linalool. A convenient preparative procedure for this final synthesis step involves passing the 1,5-dimethylcyclooct-1-en-5-ol, optionally mixed with a diluent such as an alkane or nitrogen, through a tube heated to 500° to 550° C.

The acetate ester of 1,5-dimethylcyclooct-1-en-5-ol is itself of interest as aroma chemical since it possesses an attractive woody odor. The invention therefore also includes perfume compositions containing this compound.

The invention is illustrated further in the following Examples. The NMR spectra were measured at 60 MHx in deuterochloroform solution and the results are quoted relative to a tetramethylsilane standard.

EXAMPLE I

Preparation of 1,5-dimethylcyclooct-1-en-5-ol (Procedure A)

(a) Epoxidation

A mixture containing 85% 1,5-dimethylcycloocta-1,5-diene and 15%w 1,6-dimethylcycloocta-1,5-diene (136 g), tert-butylhydroperoxide (40 g, purity 90%), a mixed titanium dioxide+silica catalyst (10 g) and cyclohexane (150 ml) were heated together under reflux for two hours. At this stage it was shown by GLC that the conversion of diene starting material was 31% with a selectivity to the required mono-epoxide of 93%. The product could be further purified by distillation, b.p. 98° C. at 20 mm Hg.

The NMR spectrum of the compound showed the following absorptions:

$\delta = 5.40$ ppm (triplet, C=CH—)
$\delta = 2.77$ ppm (triplet, >CH—O)

$\delta = 1.72$ ppm (singlet, C=$\overset{|}{C}$=CH₃)

$\delta = 1.26$ ppm (singlet, CH₃—$\overset{|}{\underset{|}{C}}$—O)

(b) Reduction (1) The crude reaction mixture from (a) (125 g) was mixed with dry ethylene diamine (200 ml) and to this mixture was added lithium metal (5.25 g) over a period of 0.5 hours. The mixture was then stirred at 30° C. for an additional one hour. Water (20 ml) was slowly added to the mixture which was then extracted with pentane. The required tertiary alcohol was isolated by distillation b.p. 180° C. at 20 mm Hg, yield 75% based on the weight of epoxide in starting material.

(2) The reduction of the epoxide was also carried out using sodium in liquid ammonia at −33° C. The yield of the tertiary alcohol was 86% based on the weight of epoxide starting material.

The NMR spectrum of 1,5-dimethylcyclooct-1-en-5-ol showed the following absorptions:

$\delta = 5.45$ ppm (triplet, =CH—)
$\delta = 1.4$—2.4 ppm (multiplets, 10 H)

$\delta = 1.17$ ppm (singlet CH₃—$\overset{|}{\underset{|}{C}}$—)
$\phantom{\delta = 1.17\text{ ppm (singlet CH}_3-\text{C}}$OH

EXAMPLE II

Preparation of 1,5-dimethylcyclooct-1-en-5-ol (Procedure B)

(a) Hydrohalogenation (1) The mixture of 1,5- and 1,6-dimethylcycloocta-1,5-dienes used in Example I (68 g) and cuprous chloride(0.68 g) was stirred under an atmosphere of hydrogen chloride gas for 3 hours at 20° C. By GLC it was shown that the conversion of starting material was 70% and the selectivity to monochlorinated material was 60%.

(2) Similarly 68 g of the mixture of 1,5- and 1,6-dimethylcycloocta-1,5-dienes used in Example I was stirred under an atmosphere of hydrogen chloride in the absence of a catalyst. Stirring was continued for 7 hours at a temperature of 50°–60° C. By GLC it was shown that the conversion of starting matertial was 93% and the selectivity to monochlorinated material was 75%, calculated on the mixture started from.

(b) Hydrolysis (1) The crude product from (a) (40 ml) was mixed with sodium hydroxide (15 g) and tri-secoctylmethylammonium chloride (0.4 g) in water (135 ml) and the mixture was stirred for 16 hours at 80° C. By GLC it was shown that the conversion of monochloride was 83% with a selectivity to 1,5-dimethylcyclooct-1-en-5-ol of 54%. The product could be isolated by distillation.

(2) A mixture of 40 ml of monochlorinated material obtained as crude product according to Example II (a) (1), solid calcium hydroxide and water in a weight ratio of 40:30:100 was stirred for 2 hours at 90° C. A complete conversion was achieved and an overall selectivity to 1,5-dimethylcyclooct-1-en-5-ol of 40% calculated on the starting material.

EXAMPLE III

Preparation of 3,7-dimethylocta-1,6-dien-3-ol

A mixture of 1,5-dimethylcylclooct-1-en-5-ol (prepared as in Example II (b) 100, cyclohexane and n-hexadecane in the volume ratio 1:2:1 was passed at a rate of 12 ml/hour together with nitrogen gas at 1/hour through a 30 cm quartz glass tube filled with 3 mm sodium glass beads at 540° C. It was shown by GLC that under these conditions the conversion of starting material was 39% and the selectivity to the required product was 87%. The alpha-linalool was recovered by distillation b.p. 91°–92° C. at 20 mm Hg.

The NMR spectrum of the compound showed the following absorptions:

$\delta = 4.9$–$6.2$ ppm (multiplet, 3H)

$\delta = 1.98$ ppm (multiplet, $-CH_2-\underset{\underset{CH_3}{|}}{C}=C$)

$\delta = 1.68$ ppm (singlet, $CH_3-\overset{|}{C}=\overset{|}{C}-$)

$\delta = 1.27$ ppm (singlet, $CH_3-\underset{\underset{OH}{|}}{\overset{|}{C}}-$)

EXAMPLE IV

Preparation of acetate ester of 1,5-dimethylcyclooct-1-en-5-ol

The mixture of 1,5- and 1,6-dimethylcycloocta-1,5-dienes was hydrohalogented as described in Example II(a) (1) and the crude mono-chloride (10 g) was heated at 60° C. with sodium acetate (12.0 g) and cuprous chloride (0.5 g) in glacial acetic acid (40 g) for 3 hours. The conversion of chloride was 82% and the required ester containing a small proportion of an isomeric acetate ester was isolated by flash distillation.

The NMR spectrum of the product showed the following absorptions:

$\delta = 5.53$ ppm (broad triplet, $-CH=C<$)

$\delta = 2.03$ ppm (singlet, $CH_3CO$)

$\delta = 1.70$ ppm (broad singlet, $=\overset{|}{C}-CH_3$)

$\delta = 1.53$ ppm (singlet, $CH_3-\overset{|}{\underset{|}{C}}-O-$)

The product possesses a pleasant woody odor.

What is claimed is:

1. A process for preparation of alpha-linalool which comprises:
    (a) epoxidizing 1,5-dimethylcycloocta-1,5-diene by reaction with an alkyl hydroperoxide in the presence of a catalyst selected from the class consisting of titanium and molybdenum to afford 5,6-epoxy-1,5-dimethyl-1-cyclooctene;
    (b) reducing the 5,6-epoxy-1,5-dimethyl-1-cyclooctene product of step (a) by reaction with an alkali metal selected from the class consisting of sodium, potassium and lithium in the presence of an amino compound selected from the class consisting of liquid ammonia, ethylene diamine, diethylamine, pyridine and hexamethylphosphoric acid triamide to form 1,5-dimethylcyclooct-1-en-5-ol; and
    (c) thermally isomerizing the 1,5-dimethylcyclooct-1-en-5-ol product of step (b) at a temperature in the range of 350° to 650° C. to afford alpha-linalool.

2. The process according to claim 1, in which the 1,5-dimethylcycloocta-1,5-diene starting material is present in a mixture of dimethyl-cyclooctadienes obtained by cyclodimerization of isoprene, said mixture containing a minor amount of 1,6-dimethylcyclooctadienes in addition to the 1,5-dimethylcycloocta-1,5-diene.

* * * * *